United States Patent [19]
Amato et al.

[11] 4,444,685
[45] Apr. 24, 1984

[54] STEREOSPECIFIC SYNTHESIS OF THIENAMYCIN FROM PENICILLIN

[75] Inventors: Joseph S. Amato, Brooklyn, N.Y.; Sandor Karady, Mountainside; Leonard M. Weinstock, Belle Mead, both of N.J.

[73] Assignee: Merck & Co., Inc., Rahway, N.J.

[21] Appl. No.: 391,032

[22] Filed: Jun. 22, 1982

Related U.S. Application Data

[63] Continuation-in-part of Ser. No. 257,695, Apr. 27, 1981, abandoned.

[51] Int. Cl.$^3$ .................. C07D 205/08; C07D 487/04; C07F 7/04
[52] U.S. Cl. .................. 260/239 A; 260/245.2 R; 260/141; 556/418
[58] Field of Search .................. 760/239 A, 245.2 R

[56] References Cited

PUBLICATIONS

Brownbridge et al., Synthesis 1983, pp. 85–104.
Chan et al., J. Amer. Chem. Soc. 102, 3534 (1980).
Andrews et al., Tet. Letters 21, 693 (1980).
Andrews et al., Tetrahedron 21, 697 (1980).
Noth et al., Chem. Berichte 93, 1078 (1960).
Mellilo et al., Tet. Letters 21, 2783 (1980).

Primary Examiner—Mark L. Berch
Attorney, Agent, or Firm—Hesna J. Pfeiffer; Daniel T. Szura

[57] ABSTRACT

A stereospecific conversion of penicillin to thienamycin, using diisopropylamine borane and magnesium trifluoroacetate to prepare the hydroxyethyl side chain and acetoacetate dianion equivalent disilylethyl to prepare the β-ketoester side chain.

9 Claims, No Drawings

STEREOSPECIFIC SYNTHESIS OF THIENAMYCIN FROM PENICILLIN

This application is continuation-in-part of U.S. application Ser. No. 257,695 filed Apr. 27, 1981, now abandoned.

The instant invention relates to a novel process for preparing the antibiotic thienamycin. More particularly, the instant invention relates to a stereocontrolled synthesis of thienamycin from penicillins.

Thienamycin is a uniquely structured and highly potent β-lactam antibiotic having the formula:

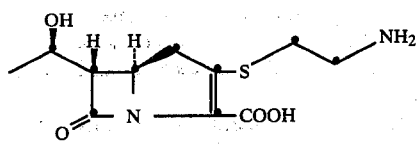

The unique structure and high potency of this compound have led to considerable synthetic activity designed to afford operable means for preparing thienamycin. Applicants have discovered an efficient stereocontrolled synthesis, employing penicillin as the starting material, which may be used as a manufacturing process.

Penicillin (6-APA) is a readily available inexpensive β-lactam antibiotic having the formula:

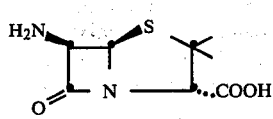

Applicants now have discovered a process whereby penicillin readily can be converted into the well-known ketoester intermediate of thienamycin having the formula:

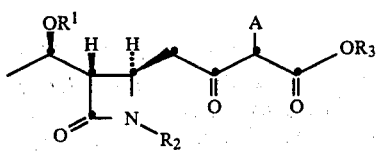

wherein $R_1$ is a readily removable hydroxy protecting group such as, for example, trimethylsilyl, t-butyldimethylsilyl, triethylsilyl, benzyl, diphenylmethyl, p-nitrobenzyl, methoxymethyl, formyl, acetyl, benzyloxycarbonyl, p-nitrobenzyloxycarbonyl and the like; $R_2$ is hydrogen or a nitrogen protecting group which, for example may be the same as $R_1$ defined above; $R_3$ is a readily removable group such as, for example, trimethylsilyl, t-butyldimethylsilyl, triethylsilyl, methyl, benzyl, p-nitrobenzyl.

The transformation of the stereochemistry of penicillins (5R, 6R) to that of thienamycin (5R, 6S, 8R) requires inversion of C-6, retention at C-5 and the establishment of a new center at C-8. The process of the instant invention whereby these results are obtained is illustrated in the following general reaction scheme.

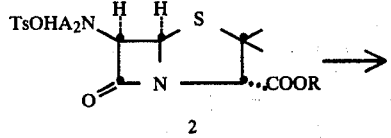

2

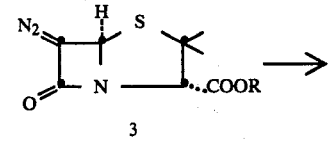

3

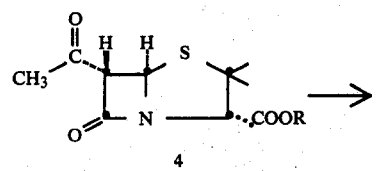

4

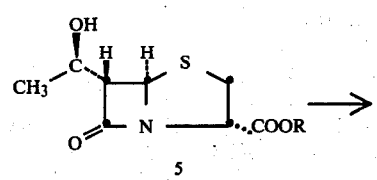

5

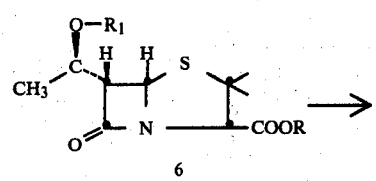

6

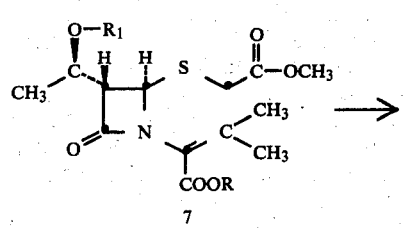

7

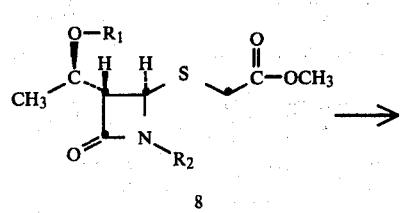

8

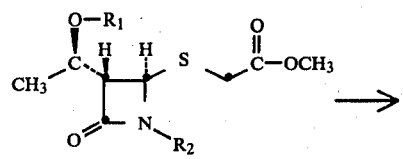

9

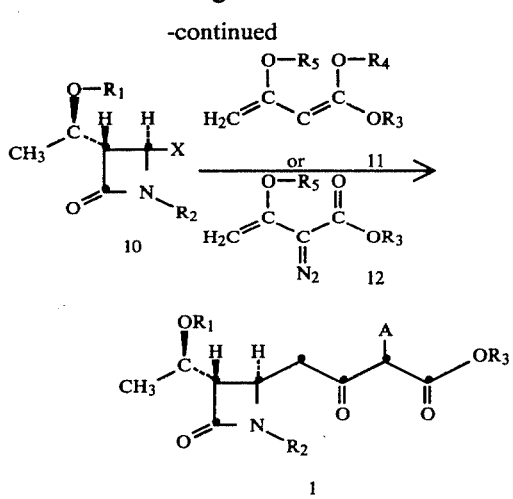

R₁, R₂, R₃ and A defined above.
R₄ and R₅ are the same as R₃ defined above.
R is hydrogen and the COOR group represents an ester.
TsOH represents tosyl.
X is Cl, Br or I.

As will be seen from the foregoing reaction scheme, the process of the instant invention involves conversion of 6-APA (2) desirably in the form of the tosyl salt of an ester thereof (conveniently, a loweralkyl or benzyl ester), into 6-diazopenicillanate (3) with sodium nitrite in the presence of p-toluene sulfonic acid. The 6-diazopenicillanate then is treated with excess acetaldehyde and a catalytic amount of $ZnCl_2$ at $-15°\text{--}15°$ C. followed by extraction with aqueous $H_3PO_4$ to obtain β-acetyl penicillanate (4). Although $ZnCl_2$ is the preferred catalyst, other Lewis Acids such as, for example, $AlCl_3$, $BF_3$ and $TiCl_4$ may be used.

Reduction of the 6-acetyl penicillanate stereospecifically with diisopropylamine borane and magnesium trifluoroacetate trifluoroacetic acid solvate in ether at $-20°\text{--}9°$ for 60 to 90 minutes yields the desired R, S, R alcohol (5) in 75% yield. The bulky amine borane and the chelating agent are essential to achieve stereospecifity. Although diisopropylamine borane and magnesium are preferred other amine boranes, such as for example, diphenylamine borane, diethylamine borane, dicyclohexylamine borane, and other chelating agents derived from Lewis acids such as for example, the salts of Al, B, Fe and Zn with acids such as trifluoroacetic acid, acetic acid, hydrochloric acid, hydrobromic acid, methylsulfonic acid, phenylsulfonic acid and the like, can be employed.

After protecting the hydroxyl group of the alcohol (5), for example by silylation, the hydroxy protected intermediate (6) is treated with methyl bromoacetate and t-butoxide to open the thiazoline ring to yield the azetidin-2-one (7). Other alkylating agents such as methyliodide, benzyl bromide and other strong bases can be employed. The reaction conveniently is carried out at room temperature and usually is complete in 3–6 hours. Permanganate oxidation of (7) in pyridine and water at room temperature for 4 hours yields the β-lactam intermediate (8) which then may be N-protected, by silylation with t-butyldimethylsilyl chloride for example, to yield intermediate (9) which, upon halogenolysis with Cl, Br and I or sulfonyl chloride in carbon tetrachloride, yields intermediate (10).

The β-ketoester side chain then is introduced by treating intermediate (10) with synthons (11) or (12), wherein R₄ and R₅ are the same as R₃ defined above. The reaction may be carried out by dissolving equimolar quantities of (10) and synthons (11) or (12) in acetonitrile and adding $AgBF_4$, or other Lewis acids such as mercury trifluoroacetate, titanium tetrachloride, zinc iodide, silver per-chlorate, at 0° C. The β-ketoester intermediate (1) is obtained. Conversion of these intermediates to thienamycin proceeds techniques already described in the literature (see Melillo, et al., Tet. Letters, 21, 2783–2786, 1980.

Synthon (11) is prepared by the method of Chan et al., J.A.C.S., 102–10, 3534 (1980). Synthon (12) is a new compound. H is prepared by naphthalene sulfonylazide diazo exchange reaction with benzylacetoacetate to obtain benzyl 2-diazoacetoacetate which then is sylated with hexamethyldisalazine and trimethylsilyl chloride.

The best mode contemplated by applicants for carrying out their invention is set forth in the following working examples. No limitation, however, is intended except as set forth in the appended claims.

EXAMPLE 1

Benzyl 6-α-Acetylpenicillanate

Step A: Benzyl 6-Diazopenicillanate

To a slurry of 8.0 g of tosyl salt of 6-APA benzyl ester in 100 mls of methylene chloride at 15° C. is added a solution of 3 gms. of sodium nitrite in 50 mls of water followed by 1 gm p-toluene sulfonic acid. The mixture is stirred for 15 min. then another 1 gm p-toluene sulfonic acid is added, and the mixture stirred another 15 min. at +15° C. The methylene chloride cut is removed and the aqueous layer extracted with methlene chloride. The combined organics are washed with saturated sodium bicarbonate and 1X sodium chloride, and dried over $MgSO_4$. The mixture is filtered through a 1" pad of silica gel and washed with methylene chloride. The mixture is then concentrated in vacuo to 100 mls, and redried with $MgSO_4$.

Procedure and characterization: D. Hauser and H. P. Sigg, Helv. Chem. Acta, 50, 1327 (1967)

Step B: Benzyl 6-α-Acetylpenicillanate

To solution A is added 10 mls of acetaldehyde cooled to $-78°$ C. followed by 4 mls. of $ZnCl_2$ in THF (5 g $ZnCl_2$ in 150 mg THF). The reaction mixture is warmed very slowly to 15° C., and extracted 1X with ice cold 1:3 $H_3PO_4$:$H_2O$, 1X ice cold NaCl, dried over $MgSO_4$ and concentrated in vacuo. The residue is dissolved in 50 mls diethylether.

¹HNMR: ($CDCl_3$) 60 MN 1.3 (s, $CH_3$), 1.5 (s, $CH_3$) 2.2 (s, $CH_3CO$), 4.2 (d, 1H, J-2 Hz, $C_6$—H), 4.4 (s, 1H, $C_3$—H), 5.1 (s, 2H, O—$CH_2$), 5.6 (d, 1H, J-2 Hz, $C_5$—H), 7.3 (s, 5H, Ar).

EXAMPLE 2

Benzyl 6-α-[(R)-1'-Hydroxyethyl]penicillanate

To a solution of 20 mm of magnesium trifluoroacetate trifluoroacetic acid solvate in 30 mls. of diethylether at $-78°$ C. is added 2 mm of the 6-acetyl penicillanate of Example 1 dissolved in 20 mls. of diethylether. To this is added 400 mg of diisopropylamineborone in 10 mls diethylether. The solution is warmed to 0° C. and stirred for about 75 minutes. To this is added 1:3

HCl:H₂O, extracted 3X with diethylether. The combined organic extracts are washed with saturated NaHCO₃ to pH8, washed with saturated NaCl, dried over MgSO₄, concentrated in vacuo, and purified by preparative chromatography.

¹H NMR (Acetone-d₆, 100 MHz) 1.28 (d, 3H, J=6H₂, CHCH₃ 1.41 and 1.61 (s, 3H, CH₃), 3,26 (dd, 1H, J=7 and 1.8 Hz, C₆—H) 4.20 (m, 1H, C₇—H), 4.49 (s, 1H, C₃—H), 5.24 (s, 2H, OCH₂—), 5.33 (d, 1H, J=1.8 Hz, C₅—H), 7.45 (m, 5H, Ar).

EXAMPLE 3

Benzyl 6-α[(R)-1′-t-Butyldimethylsilyloxyethyl]penicillanate

To a solution of 4.0 g (11.7 mm) of the 6-hydroxyethyl compound prepared as in Example 2, in DMF at 0° C., was added a solution of t-butyldimethylsilyl chloride in DMF followed by 1.9 mls of triethylamine. Total volume of DMF is 25 mls. The solution is warmed to room temperature, and stirred for 4 hours. The mixture is poured into water and extracted with diethylether. The organic phase is washed with water, dried with sodium sulfate and concentrated to yield and oil.

¹H NMR (CDCl₃, 60 MH₂) 0.2 (s, 9H, SiCH₃), 1.0 (s, 6H t Bu), 1.35 (d, 3H, J=6 Hz CH₃—CH—O), 1.45 and 1.70 (s, 3H, CH₃), 3.3 (dd, 1H, J=5, and 1.5 Hz C₇—H), 4.35 (m, 1H, CH—O), 4.50 (s, 1H, C₃—H) 5,22 (s, 2H, CH₂O), 5.32 (d, 1H, J=1.5 Hz, C₇—H), 7.4 (s, 5H, Ar)

EXAMPLE 4

(3S, 4R)-3-[(R)-1′-t-Butyldimethylsilyloxyethyl]-4-(methoxycarbonylmethylthio)azetidin-2-one

Step A: (3S, 4R)-1-(1-Benzyloxycarbonyl-2-methylprop-1-enyl)-3-[(R)-1′-t-butyldimethylsiloxy ethyl]-4-(methoxycarbonylmethylthio)-azetidin-2-one To a solution of 2.0 g (4.69 mm) of the silylated penicillin prepared as in Example 3 and 830 mg (5 mm) methylbromoacetate in 10 ml t-butanol and 10 ml tetrahydrofuran at 0° C., is added to a solution of 560 mg (48 mm) potassium t-butoxide in 5 ml of t-butanol and tetrahydrofuran, over 40 minutes. The solution is warmed to room temperature, and stirred for 4 hours, then it is poured into NaCl solution, extracted with methylene chloride; the combined organic extracts are dried over MgSO₄ and concentrated in vacuo to yield 2.6 g.

¹H NMR (CDCl₃, 60 MHz) δ, 1.35 (d, 3H, J=6 Hz, CH₃—CH—O) 2.05 and 2.35 (s, 3H, CH₃), 3.15 (d, 1H, J=3 Hz, (C₃—H) 3.25 (s, 2H, S—CH₂—), 3.75 (s, 4H, OCH₃ and C₄H), 4.2 (m, 1H, CH—O).

Step B: (3S, 4R)-3-[(R)-1′-t-Butylidimethylsilyloxyethyl]-4-(methoxycarbonylmethylthio) azetidin-2-one To the 2.6 g (4.6 mm) from Step A in 35 ml pyridine and 5.8 ml water is added 750 mg (4.6 mm) potassium permanganate in portions and the solution stirred under nitrogen for 2 hours. The mixture is poured into water, and methylene chloride added. SO₂ gas is introduced until a colorless solution is obtained. The organic extract is washed with dilute HCl, NaHCO₃, NaCl, dried and concentrated in vacuo. The product is isolated by preparative chromatography.

¹H NMR (CCl₄, 60 MHz) δ1.2 (d, 3H, J=7 Hz, CH₃—CH—O) 3.1 (dd, 1H, J=4, 2 Hz, C₃—H), 3.3 (s, 2H, S—CH₂) 3.7 (3H, MeO), 4.2 (qd, 1H, J=7 and 4 Hz, CH₃—CH—O), 4.8 (d, H, J=2 Hz, C₄—H), 7.4 (s, 1H, NH).

EXAMPLE 5

(3S, 4R)-1-(t-Butyldimethylsilyl)-3-[(R)-1′-t-butyldimethylsilyloxyethyl]-4-chloroazetidin-2-one To an ice cold solution of 600 mg (1.89 mm) of the intermediate prepared as in Example 4 in 2 ml DMF, is added 360 mg of t-butyldimethylsilylchloride followed by 350 mg of triethylamine at 0° C. and the mixture warmed to room temperature and stirred for 4 hours. The mixture is poured into H₂O, extracted with diethylether, the extracts washed with H₂O, dried over MgSO₄, and concentrated in vacuo to yield 500 mg.

This solution in 10 ml carbon tetrachloride at 0° C. is kept under nitrogen and a solution of chlorine (2.4 mm Cl₂ in CCl₄) is added dropwise over 20 minutes. The solution is warmed to room temperature, and extracted with 2.5 N NaOH followed by dil NaCl solution. Drying and evaporation yields the chloro compound.

NMR (CDCl₃, 60 MHz) δ1.2 (d, 3H, J=6 Hz, CH₃CHO), 3.3 (m, 1H, C₃—H), 4.1 (m, 1H, CH₃—CH—O) 5.5 (d, 1H, J=2 Hz, C₄—H).

EXAMPLE 6

1-Methoxy-1,3-bis-(trimethylsilyloxy)buta-1-3-diene

To diisopropylamine (6.8 ml, 48 mm) in THF at 0° C. is added 30 ml of 1.6 M n-butyllithium (48 mm), then 6.5 ml tetramethylethylenediamine (TMEDA, 48 mm) cooled to −78° C. Then 7.6 g (40 mm) of methyl 3-trimethylsilyloxybut-2-enoate is added over 5 minutes at −70° C. The mixture is stirred at −75° for 10 minutes, then 8 ml (48 mm) trimethylsilylchloride is added over 5 minutes at −75° C. The solution is warmed to room temperature and concentrated in vacuo. The residue is slurried in 500 ml of n-hexane, and solids filtered off. The filtrate is concentrated in vacuo, B.P.=75°-76° C. at 0.3 mm Hg.

Procedure and characterization: Chan et al., J.A.C.S., 102-10, 3534 (1980).

EXAMPLE 7

1-Benzyloxy-1,3-bis-(trimethylsilyloxy)buta-1,3-diene

Employing the procedure of Example 6, but substituting an equivalent quantity of benzyl 3-trimethylsilyloxybut-2-enoate for the methyl ester, the title product is obtained.

¹HNMR (CDCl₃, 60 MHz) δ0, 25 (two s, 9H, SiCH₃) 4.05 and 4.18 (s, 1H, X—CH₂), 4.5 (s, 1H, —CH═)

EXAMPLE 8

(3S, 4R)-1-(t-Butyldimethylsilyl)-3-[(R)-1′-t-butyldimethylsilyloxyethyl]-β, 2-dioxo-4-azetidinebutanoic Acid Methyl Ester To the product of Example 5 (1.6 mm) in 10 ml of acetonitrile is added 2 ml of the silyl reagent (9 mm) prepared in Example 6. The solution is cooled to 0° C. and a solution of 1 gm AgBF₄ in 10 ml acetonitrile added over 20 minutes. The solution is warmed to room temperature, poured into NaCl solution and CH₂Cl₂; the AgCl filtered off and the extract is dried and concentrated.

¹H NMR (CDCl₃, 100 MHz) δ0, 05 and 0.07 (s, 3H, OSiMe), 0,20 and 0,21 (s, 6H, NSiMe), 0, 88 and 0, 96 (s, 9H, BuSi), 1.18 (d, 3H, J=6.3 Hz, CH₃—CH—O), 2.87 (dd, 1H, J=4.4 and 2.8 Hz, C₃—H), centered at 2.9 (m, 2H, ABX, 2j=17.0 Hz, 3j=8.2 and 4.7 Hz, HC₄—CH₂), 3.46 (s, 2H, —CO—CH₂CO—), 3.75 (s, 3H, OMe), 4.0 (ddd, 1H, ABX, J=8.2, 4.7, 2.8 Hz, C₄—H), 4.18 (qd, 1H, J=6.3, 4.4 Hz, CH₃—CH—O).

¹³C NMR (CDCl₃, int TMS) δc 22.3 (CH₃—C—O), 47.5 (C₄), 48.9 and 49.6 (CH₂CO), 65.5 and 65.6 (C₃ and CH₃—CHO) 167.1 (COOMe) 172.8 (C₂), 199.5 (CH₂—CO).

Evidence of enol form is seen in both 13C and ¹H NMR spectra.

EXAMPLE 9

(3S, 4R)-1-(t-Butyldimethylsilyl)-3-[(R)-1'-t-butyldimethyl-silyloxyethyl]-β, 2-dioxo-4-azetidinebutanoic Acid Benzyl Ester Employing the procedure of Example 8, but substituting an equivalent quantity of the silyl reagent prepared in Example 7, the title product is obtained.

¹³C NMR (CDCl₃, int-TMS) δc 22.2 (CH₃—C—O) 47.3 (C₄), 48.7 and 49.7 (CH₂CO), 65.5 (C₃ and CH₃ CHO), 67.1 (O—CH₂—O), 172.6 (C₂), 199.3 (CH₂CO).

EXAMPLE 10

1-Benzyloxy-1-oxo-2-diazo-3-(trimethylsilyloxy)butene

Step A: Benzyl-2-diazoacetoacetate

To a solution of benzylacetoacetate (14.5 g, 75.5 mm) and 2-naphthalene sulfonylazide (19.2 g, 82.5 mm) in 100 ml of acetonitrile, add dropwise triethylamine (11.2 ml, 80 mm) and stir for 12 hours. Dilute with ether and filter. Extract the filtrate with dilute phosphoric acid and then with saturated sodium bicarbonate solution. Dry over magnesium sulfate and evaporate to obtain 14.7 g of the title product which is employed directly in the next step.

Step B: 1-Benzyloxy-1-oxo-2-diazo-3-(trimethylsilyloxy)butene

To a solution of lithium hexamethyldisilazide (25 mm) in 200 ml of tetrahydrofuran, prepared by the method of Example 6, add tetramethylethylenediamine (5.2 ml, 20 mm) and benzyl diazoacetate (4.4 g, 20 mm) at −78° C. After five minutes, add trimethylsilyl chloride (4 ml, 25 mm) and allow the mixture to warm to room temperature. Add hexane to precipitate the salts. Remove the precipitate by filtration. Concentrate the filtrate to obtain the title product as an oil (5.7 g).

¹HNMR (CDCl₃, 60 MHz) δ4.2 and 5.0 (d, 1H, J=2 Hz, C═C—H), 5.2 (S, 2H, O—CH₂—), 7.4 (S, 5H, Ar).

EXAMPLE 11

(3S, 4R)-1-(t-Butyldimethylsilyl)-3-[(R)-1'-t-butyldimethyl-siloxyethyl]-α-diazo-β,2-dioxo-4-azetidinebutanoic Acid Benzyl Ester Employing the procedure of Example 8 but substituting an equivalent quantity of the silyl reagent prepared in Example 10, the title product is obtained.

¹Hnmr ((CDCl₃) 60 MHz (0.25. 12H, SiCH₃), 0.8(S, 18H, tBu), 1.39 (d, 3 J=6.2, CH₃), 1.8 (d, 1, OH), centered at 2.68 (ABX, 2, J=6.8, 7.6 and 18.9), 3.17 (d, d, 1.2 and 7.2), 4.14 (ABX, 1, J=1.9 and 7.3, H₅), 4.31 (dq, J=6.2 and 7.2 CHO), 4.72 (S, 1, ═C—H), 5.21 (S, 2, COO CH₂ Ph and 7.36 (S, 5, Ph)

Although the foregoing description has related specifically to the sterospecific conversion of penicillin to thienamycin wherein the intermediate, 6-acetyl penicillanote, is stereospecfically reduced with diisopropylamine borane and magnesium trifluoroacetate to obtain the desired R, S, R alcohol, it will be obvious to those skilled in the art from a study this description that the described reduction is one of general application and is not limited in application to S-bound intermediates as illustrated above. Included among such applications, for example, is the preparation of (7R, 3S, 4R) 1-(t-butyl-dimethylsilyl)-3-(1-hydroxyethyl)-4-vinylazetidin-2-one from (3S, 4R) 1-(t-butyldimethylsilyl)-3-acetyl-4-vinylazetidin-2 one. Applicants have found that treatment of the acetyl intermediate with diisopropylamine borane and magnesium trifluoroacetate affords essentially the desired 7R, 3S, 4R alcohol. Both the starting material and the product, a useful intermediate in thienamycin synthesis, are described in the literature (see A. F. Bouffard, B. G. Christensen, J. Org. Chem., 46, 2208–2212 (1981). The following example illustrates this application.

EXAMPLE 12

(7R, 3S, 4R) 1-(t-Butyldimethylsilyl)-3-(1-hydroxyethyl)-4-(vinylazetidin-2-one

To a solution of (3S, 4R)-1-(t-butyldimethylsilyl)-3-acetyl-4-vinylazetidin-2-oe (85 mg)* in ether (5 ml) was added magnesium trifluoroacetate (425 mg). The solution was cooled to −78° C. and a solution of diisopropylamine borane (80 mg) in ether (1 ml) was added. The mixture was warmed to 0° C. and stirred in an ice bath for one hour. After this, 3 ml of 90% hydrochloric acid was added and the mixture was allowed to stand for 15 minutes. Partition between methylene chloride and water followed by drying and evaporation afforded on oil. The product was isolated by chromotography on silica gel; elution with methylene chloride 20% ethylacetate. NMR spectra indicated that only the R, S, R isomer was present.

*F. A. Bouffard, B. G. Christensen, J. Org. Chem., 46, 2208, 2212 (1981).

IR(CH₂Cl₂) 5.79 μm; NMR (CDCl₃) δ0.17 and 0.23 (2S, Si(CH₃)₂), 0.98 (s,t-BuSi), 1.23 (d, J=6 Hz, CH₃CH), 2.93 (m, H₃ and OH), 3.8–4.4 (m, H₄ and CH₃CH), 5.1–6.3 (m, CH═CH₂).

The subject matter which applicants regard as their invention is particularly pointed out and distinctly claimed as follows:

What is claimed is:

1. A process for preparing a compound of the formula

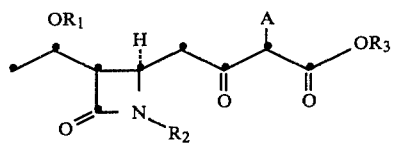

wherein
R₁ is a hydroxy protecting group selected from the group consisting of trimethylsilyl, t-butyldimethylsilyl, triethylsilyl, benzyl, diphenylmethyl, p-nitrobenzyl, methoxymethyl, formyl, acetyl, benzyloxycarbonyl and p-nitrobenzyloxycarbonyl;

$R_2$ is hydrogen or a nitrogen protecting group selected from the group consisting of $R_1$;

$R_3$ is a member selected from the group consisting of trimethylsilyl, t-butyldimethylsilyl, triethylsilyl, methyl, benzyl, p-nitrobenzyl; and A is $H_2$ or $=N_2$;

which comprises the steps of (a) treating 6-APA with sodium nitrite in the presence of p-toluenesulfonic acid to obtain 6-diazopenicillanate;

(b) treating the 6-diazopenicillanate with excess acetaldehyde and a catalytic amount of Lewis acid to obtain 6-acetylpenicillanate;

(c) reducing the 6-acetylpenicillanate with an amine borane selected from the group consisting of diethylamine borane, diisopropylamine borane, diphenylamine borane and dicyclohexylamine borane, and a chelating agent selected from magnesiumtrifluoroacetate trifluoroacetic acid solvate and Lewis acid derivatives which are salts of Al, B, Fe and Zn with trifluoroacetic acid, acetic acid, hydrochloric acid, hydrobromic acid, methylsulfonic acid phenylsulfonic acid in order to obtain 6-(1-hydroxyethyl)penicillanate;

(d) treating the alcohol with a hydroxy protecting group;

(e) treating the hydroxy protected alcohol with an alkylating agent selected from methylbromoacetate, methyliodide and benzyl bromide and a strong base to open the thiazoline ring;

(f) subjecting the azetidin-2-one intermediate to permanganate oxidation to obtain the β-lactam intermediate;

(g) N-protecting the β-lactam intermediate;

(h) treating the N-protected intermediate by halogenolysis with $Cl_2$, $Br_2$, $I_2$ or sulfonyl chloride in carbon tetrachloride to obtain the 6-halo β-lactam intermediate; and (i) reacting the equimolar quantities of the 6-halo compound with a synthon selected from the group consisting of a compound of the formula:

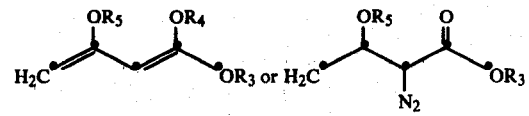

wherein $R_4$ and $R_5$ are the same or different members of the $R_3$ group as defined above, in the presence of acetonitrile and a Lewis acid and recovering the β-ketoester.

2. The process of claim 1, Step (b), wherein the Lewis acid is zinc chloride.

3. The process of claim 2 wherein the amine borane is diisopropylamine borane and the chelating agent is magnesium trifluoroacetate.

4. The process of claim 3 wherein the halogenolysis is carried out with chlorine in carbontetrachloride.

5. The process of claim 4 wherein $R_4$ and $R_5$ are trimethylsilyl and $R_3$ is benzyl.

6. A process for preparing benzyl 6-α-[(R)-1'-hydroxyethyl]penicillanate which comprises stereospecifically reducing benzyl 6-α-acetylpenicillinate with diisopropylamine borane in the presence of magnesium trifluoroacetate.

7. A process for preparing (3S, 4R)-1-(t-butyldimethylsilyl)-3-[(R)-1'-t-butyldimethylsilyloxyethyl]-β,2-dioxo-4-azetidinebutanoic acid benzyl ester which comprises reacting equimolar quantities of (3S, 4R)-1-(t-butyldimethylsilyl)-3-[(R)-1'-t-butyldimethylsilyloxyethyl]-4-chloroazetidin-2-one and 1-benzyloxy-1,3-bis-(trimethylsilyl-oxy)buta-1,2-diene in acetonitrile and adding $AgBF_4$.

8. A process for preparing (3S, 4R)-1-(t-butyldimethylsilyl)-3-[(R)-1'-t-butyldimethylsiloxyethyl]-α-diazo-β,2-dioxo-4-azetidinebutanoic acid benzyl ester which comprises reacting equimolar quantities of (3S, 4R)-1-(t-butyldimethylsilyl)-3-[(R)-1'-t-butyldimethylsilyloxyethyl]-4-chloroazetidin-2-one and 1-benzyloxy-1-oxo-2-diazo-3-(trimethylsilyloxy)butene in acetonitrile and adding $AgBF_4$.

9. A process for preparing (7R, 3S, 4R) 1-(t-butyldimethylsilyl)-3-(1-hydroxyethyl)-4-vinylazetidin-2-one which comprises stereospecifically reducing (3S, 4R) 1-(t-butyldimethylsilyl)-3-acetyl-4-vinylazetidin-2-one with diisopropylamine borane in the presence of magnesium trifluoroacetate.

* * * * *